(12) United States Patent
Canady et al.

(10) Patent No.: US 11,160,598 B2
(45) Date of Patent: Nov. 2, 2021

(54) CERAMIC TIP FOR GAS-ASSISTED ELECTROSURGICAL PROBE

(71) Applicant: U.S. Patent Innovations, LLC, Takoma Park, MD (US)

(72) Inventors: Jerome Canady, Lakeland, FL (US); Feng Yan, Fairfax, VA (US); Taisen Zhuang, Rockville, MD (US)

(73) Assignee: US Patent Innovations, LLC, Takoma Park, MD (US)

( * ) Notice: Subject to any disclaimer, the term of this patent is extended or adjusted under 35 U.S.C. 154(b) by 830 days.

(21) Appl. No.: 15/833,780

(22) Filed: Dec. 6, 2017

(65) Prior Publication Data
US 2019/0167334 A1 Jun. 6, 2019

(51) Int. Cl.
*A61B 18/04* (2006.01)
*A61L 31/02* (2006.01)
*A61B 18/14* (2006.01)
*A61B 18/00* (2006.01)

(52) U.S. Cl.
CPC ........ *A61B 18/042* (2013.01); *A61L 31/026* (2013.01); *A61B 2018/00083* (2013.01); *A61B 2018/1417* (2013.01); *A61B 2218/005* (2013.01)

(58) Field of Classification Search
CPC ............. A61L 31/026; A61B 18/042; A61B 2018/00083; A61B 2218/005
See application file for complete search history.

(56) References Cited

U.S. PATENT DOCUMENTS

| | | | |
|---|---|---|---|
| 4,040,426 A | 8/1977 | Morrison | |
| 4,781,175 A | 10/1988 | Ozaki | |
| 5,207,675 A | 5/1993 | Canady | |
| 6,197,026 B1 | 3/2001 | Farin | |
| 6,733,496 B2* | 5/2004 | Sharkey | A61B 18/1492 128/898 |
| 9,603,653 B2 | 3/2017 | Schnitzler | |
| 2006/0079873 A1* | 4/2006 | Scopton | A61B 17/3478 606/37 |
| 2007/0149970 A1* | 6/2007 | Schnitzler | A61B 18/042 606/49 |

* cited by examiner

*Primary Examiner* — Linda C Dvorak
*Assistant Examiner* — Annabeth E Rodriguez
(74) *Attorney, Agent, or Firm* — 24IP Law Group USA, PLLC; Timothy Dewitt

(57) ABSTRACT

An apparatus for gas-assisted electrosurgery having a gas-assisted electrosurgical probe comprising a tube and an electrode within said tube, wherein a distal end portion of said electrode extends from an opening at a distal end of said tube and an electrically insulating tip connected to a distal end of said electrode. The electrically insulating tip has a substantially hemispherical distal end portion having a radius $r_1$ and a proximal portion having a circular cross-section and a central axis of a length $l_1$, wherein $l_1 > r_1$.

9 Claims, 10 Drawing Sheets

CERAMIC TIP FOR GAS-ASSISTED ELECTROSURGICAL PROBE

CROSS-REFERENCE TO RELATED APPLICATIONS

None.

STATEMENT REGARDING FEDERALLY SPONSORED RESEARCH OR DEVELOPMENT

None.

BACKGROUND OF THE INVENTION

Field of the Invention

The present invention relates to gas-assisted electrosurgical probes for use in minimally invasive surgery, and more particularly, to ceramic tips for gas-assisted electrosurgical probes.

Brief Description of the Related Art

Controlling or arresting blood loss is of high priority during surgery so as to avoid or minimize the necessity of introducing foreign blood or blood products into a patient. Standard means for controlling traumatic and surgical blood loss are electrosurgical generators and lasers, which respectively direct high-frequency electrical currents or light energy to localize heat in bleeding vessels so as to coagulate the overlying blood and vessel walls.

Argon beam coagulators additionally have been demonstrated to be effective tissue coagulators. Examples of argon beam coagulators for use in open surgery can be found in U.S. Pat. No. 4,040,426 to Morrison and U.S. Pat. No. 4,781,175 to McGreevy. Argon beam coagulators for use rigid and flexible endoscopy also are known. An example of a device for flexible endoscopy may be seen in U.S. Pat. No. 5,207,675 to the present inventor.

Various devices have been introduced for directing plasma coagulation, including side-fire probes that direct flow of an inert gas out of the end of a probe at a 90 degree angle relative to the central axis of the probe (see U.S. Pat. No. 6,197,026) and directional probes that direct the flow of inert gas at other angles relative to the central axis. Various devices also have included ceramic tips for endoscopic gas-assisted electrosurgical probes to prevent the electrodes in such probes from sticking to tissue during treatment. The ceramic tips commonly have been attached to, or inserted into, the distal end of an endoscopic probe such that the during argon plasma coagulation the electrode does not protrude out of the endoscopic tube, thereby preventing the electrode from touching the tissue.

U.S. Pat. No. 9,603,653 discloses a ceramic tip for gas-assisted electrosurgical probe where the ceramic tip is secured to the electrode rather than to the endoscopic tube. In this manner, the electrode extends out of the endoscopic tube but is prevented from touching the tissue by the ceramic tip secured to the distal end of the electrode. The ceramic tip further is described as providing a guiding function such that it directs the flow of a supplied inert gas and "guides" the plasma. Three variations are disclosed for the shape of the ceramic tip: a sphere, a concave inner section opposite the outlet of the gas-delivering device and a flat distal end, and a concave inner surface section opposite the outlet of the gas-delivering device and a hemispherical end.

SUMMARY OF THE INVENTION

In a preferred embodiment, the present invention is a probe for gas-assisted electrosurgery. The probe comprises a tube and an electrode within said tube, wherein a distal end portion of said electrode extends from an opening at a distal end of said tube and an electrically insulating tip connected to a distal end of said electrode. The electrically insulating tip may comprise a ceramic tip. The electrically insulated tip comprises a substantially hemispherical distal end portion having a radius $r_c$; a proximal portion having a circular cross-section and a central axis of a length $L_1$; wherein $L_1 > r_c$. The probe for gas-assisted electrosurgery may further comprise a fillet between said substantially distal end portion and said proximal portion. Still further, the proximal portion has an outer surface having a plurality of portions with at least two of said plurality of sections having a different radii of curvature. The at least two radii of curvature may decrease from a proximal end of said electrically insulating tip to said fillet.

In another embodiment, the present invention is a probe for gas-assisted electrosurgery. The probe comprises a tube and an electrode within said tube, wherein a distal end portion of said electrode extends from an opening at a distal end of said tube and an electrically insulating tip connected to a distal end of said electrode. The electrically insulated tip comprises a substantially hemispherical distal end portion having a radius $r_c$; a proximal portion having a circular cross-section and a central axis of a length $L_1$; wherein $L_1 > r_c$. The proximal portion has a straight outer surface. The proximal portion has a proximal end having a circular cross-section with a radius $r_p$ and $1.2r_p < L_1$. The proximal portion has a proximal end having a circular cross-section with a radius $r_p$ and a distal end with a radius $r_d$, wherein $r_d > 2r_p$. The proximal portion has a proximal end having a circular cross-section with a radius $r_p$ and a distal end with a radius $r_d$, wherein $$0.9 < \frac{r_d - r_p}{L_1} < 0.5.$$

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE DRAWINGS

For a more complete understanding of the present invention and the advantages thereof, reference is now made to the following description and the accompanying drawings, in which.

DETAILED DESCRIPTION OF THE PREFERRED EMBODIMENTS

Figure 1A:
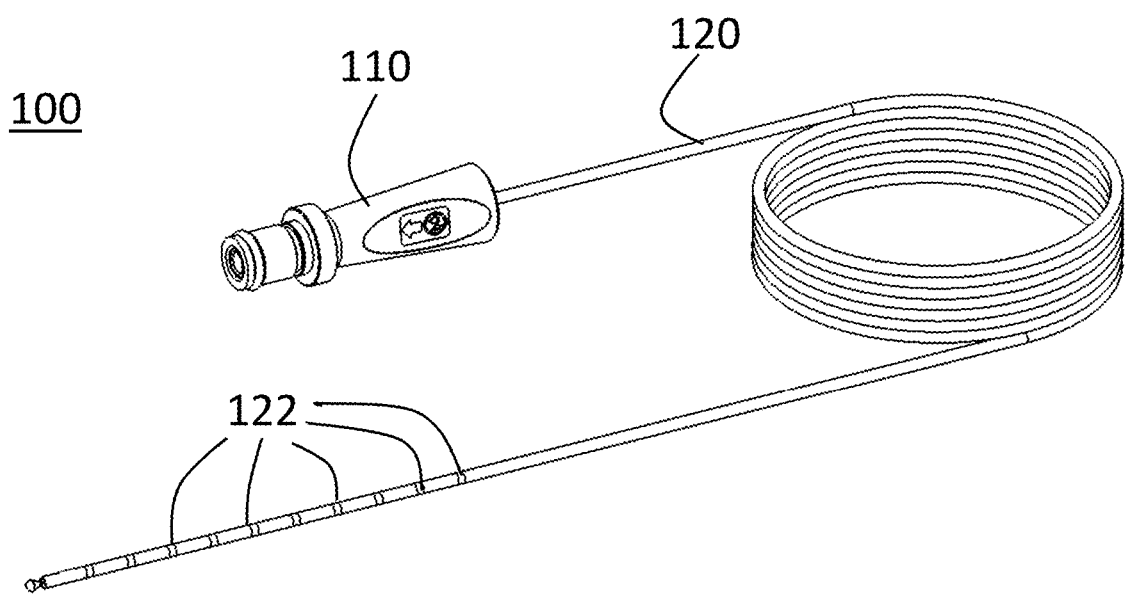
FIG. 1A is a perspective view of an endoscopic probe for a gas-assisted electrosurgical device in accordance with a preferred embodiment of the present invention.
Figure 1B:
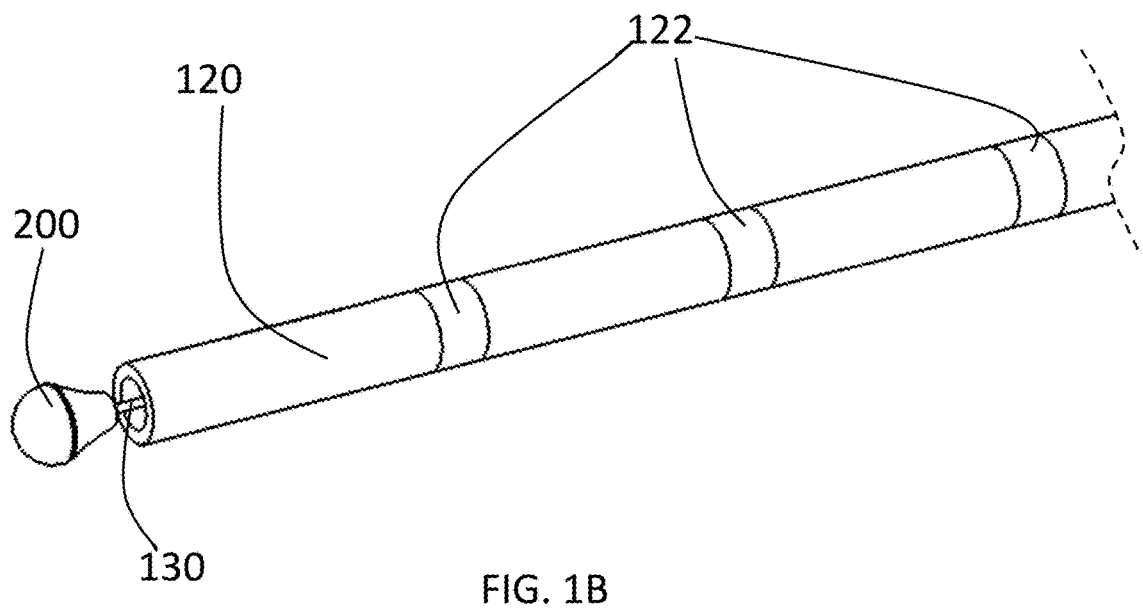
FIG. 1B is a perspective view of a distal end of an endoscopic probe for a gas-assisted electrosurgical device in accordance with a preferred embodiment of the present invention.
Figure 1C:
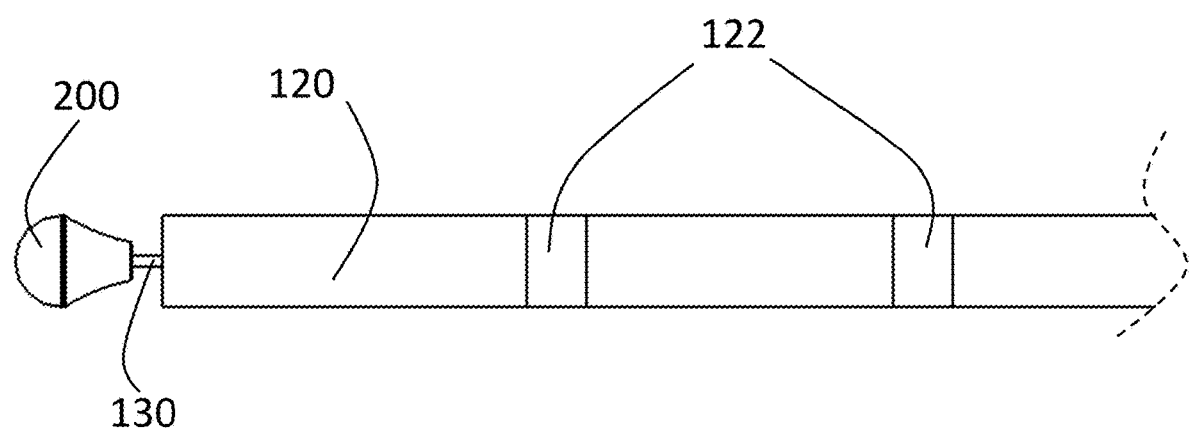
FIG. 1C is a side view of a distal end of an endoscopic probe for a gas-assisted electrosurgical device in accordance with a preferred embodiment of the present invention.
Figure 2A:
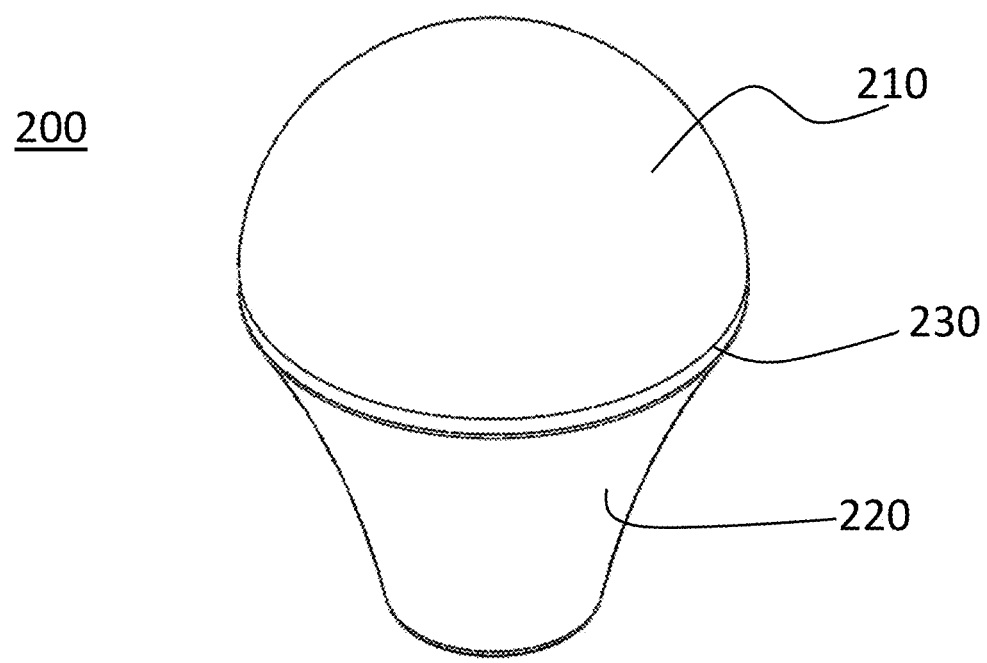
FIG. 2A is a top perspective view of a ceramic tip for a gas-assisted electrosurgical probe in accordance with a preferred embodiment of the present invention.
Figure 2B:
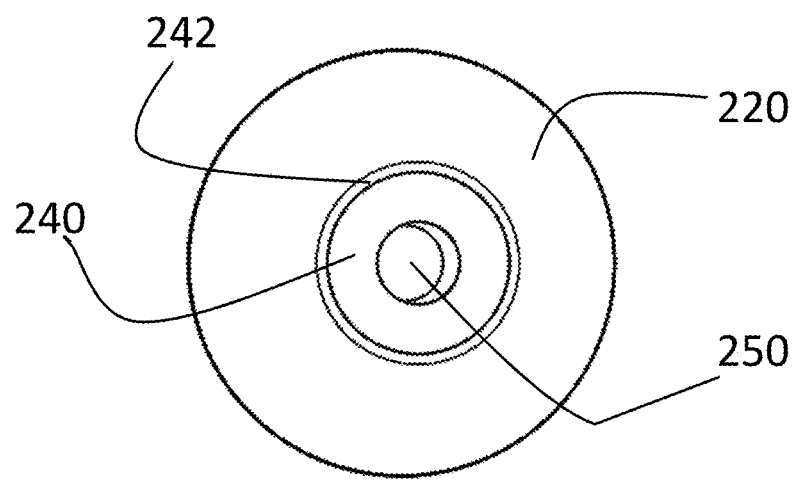
FIG. 2B is a bottom perspective view of a ceramic tip for a gas-assisted electrosurgical probe in accordance with a preferred embodiment of the present invention.
Figure 2C:
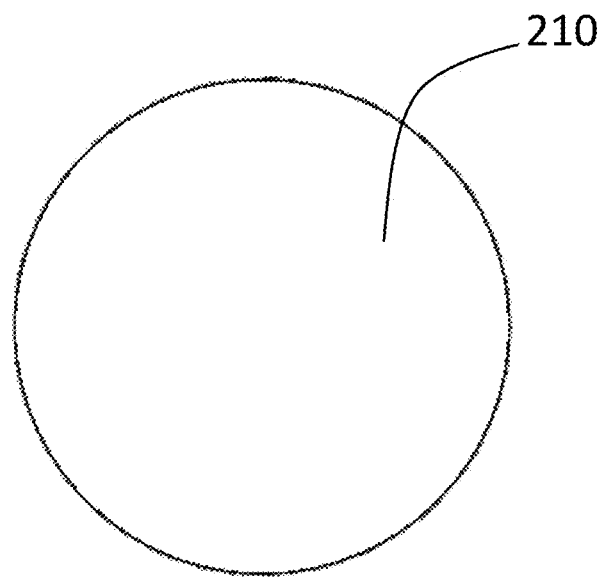
FIG. 2C is a top view of a ceramic tip for a gas-assisted electrosurgical probe in accordance with a preferred embodiment of the present invention.
Figure 2D:
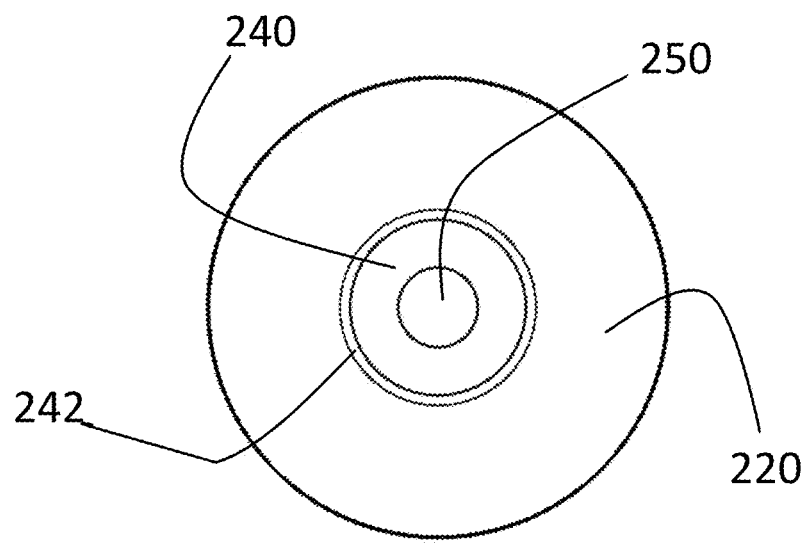
FIG. 2D is a bottom view of a ceramic tip for a gas-assisted electrosurgical probe in accordance with a preferred embodiment of the present invention.
Figure 2E:
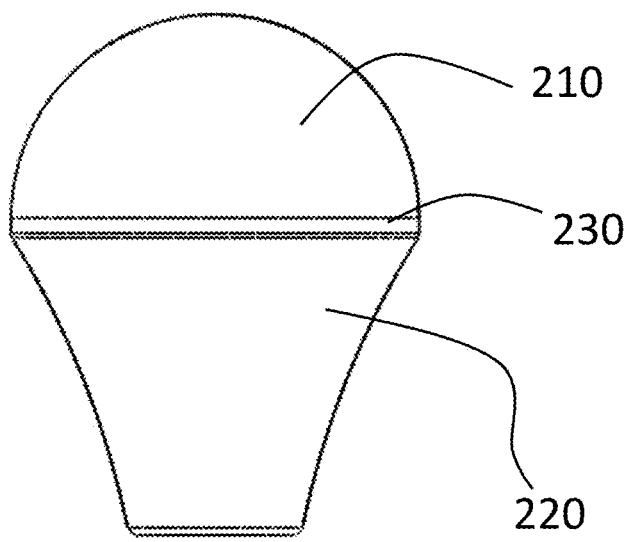
FIG. 2E is a side view of a ceramic tip for a gas-assisted electrosurgical probe in accordance with a preferred embodiment of the present invention.
Figure 2F:
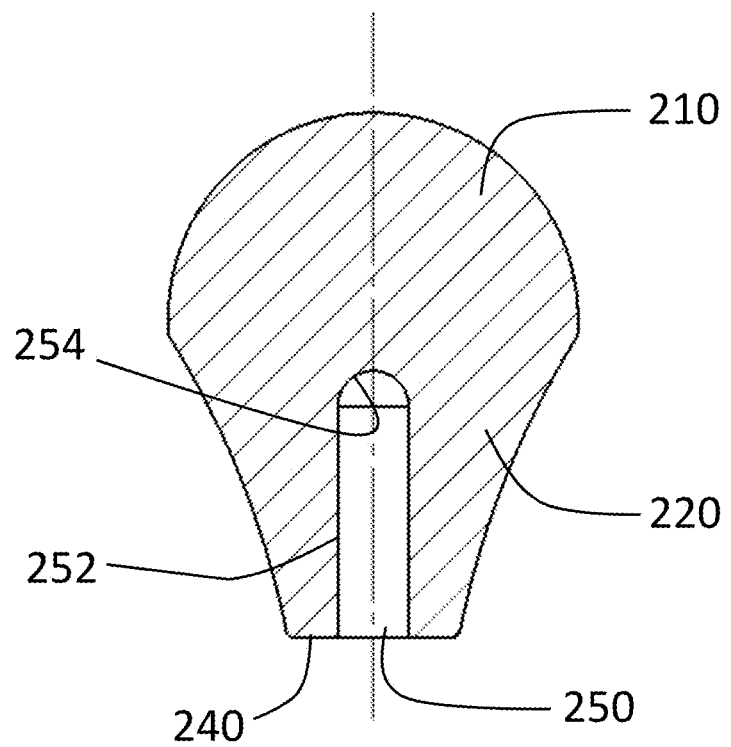
FIG. 2F is a side cross-sectional view of a ceramic tip for a gas-assisted electrosurgical probe in accordance with a preferred embodiment of the present invention.

As shown in FIGS. 1A-1C, the present invention relates to a probe for gas-assisted electrosurgery. The probe shown in FIG. 1 is for endoscopic use, but the present invention works equally well for other types of minimally invasive surgery, including but not limited to, laparoscopy and colonoscopy. An exemplary probe 100 has a plug 110, an elongated flexible tube 120 having a plurality of spaced markings 122 near its distal end, and electrode 130 and an electrically insulating tip 200, for example, a ceramic tip, on the end of the electrode. While a flexible tube 120 is shown in FIGS. 1A-1C, the present invention is by not limited to probes with flexible tubes as it works equally well with probes having rigid tubes.

A first embodiment of a ceramic tip 200 in accordance with a preferred embodiment of the present invention is described with reference to FIGS. 2A-2F. The ceramic tip 200 has a distal portion 210, a proximal portion 220 and a fillet or rounded portion 230 in between the distal and proximal portions. The distal portion preferably is hemispherical in shape. The proximal end of the ceramic tip 200 has a flat circular portion 240, a fillet or rounded portion 242 and an opening 250 for receiving a distal end of an electrode. The opening 250 is a cylindrical channel 252 having a rounded end 254.

Figure 3:
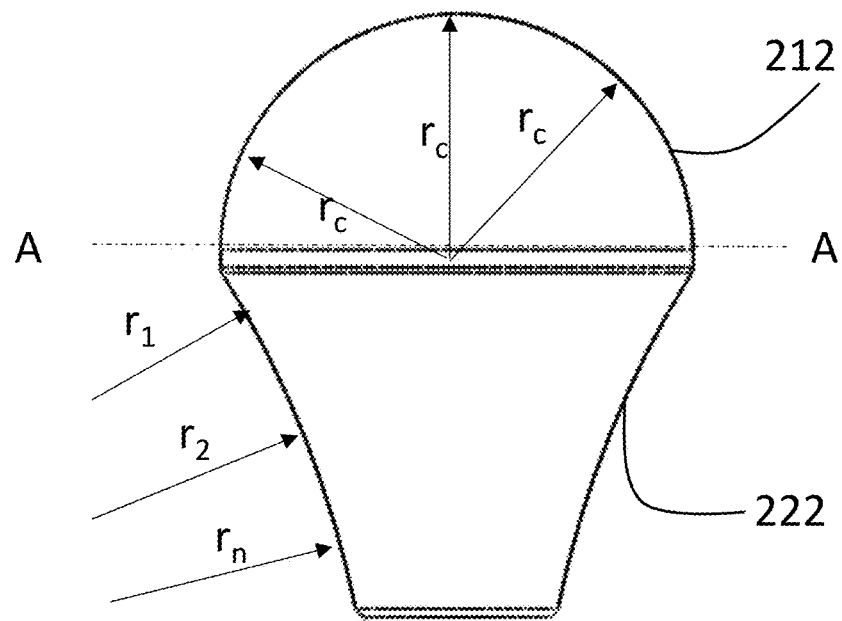
FIG. 3 is a first side dimension view of a ceramic tip for a gas-assisted electrosurgical probe with dimensional references in accordance with a preferred embodiment of the present invention.

As shown in FIG. 3, the hemispherical portion 210 above the plane identified by the line A-A has a surface 212 having a constant radius of curvature $r_c$. The proximal portion 220 is conical in shape with its surface 222 having a plurality of different radiuses of curvature $r_1, r_2, \ldots r_n$. Preferably the radii of curvature comply with the relationship $r_1 < r_2 < r_n$ to provide improved flow of plasma from the opening at the distal end of the tube 120 and around the ceramic tip 200.

Figure 4:
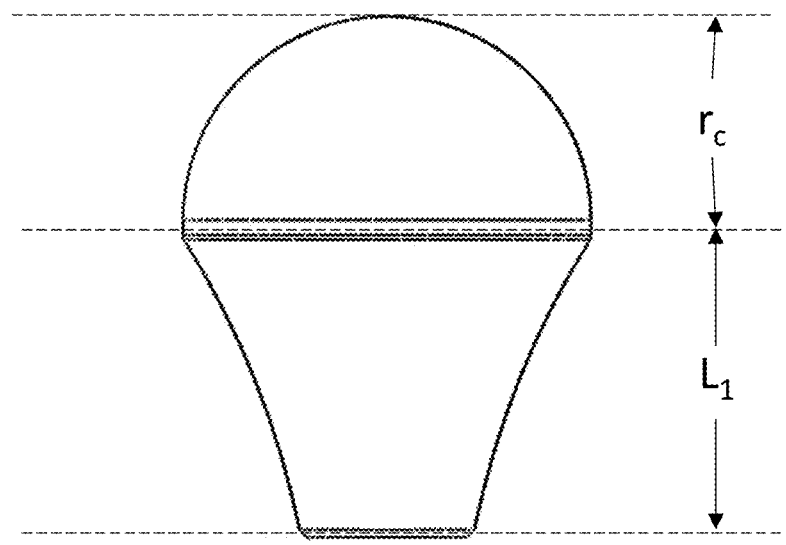
FIG. 4 is a second side view of a ceramic tip for a gas-assisted electrosurgical probe with dimensional references in accordance with a preferred embodiment of the present invention.

As shown in FIG. 4, the length $L_1$ of the central axis of the proximal portion 220 of the ceramic tip 200 (from the proximal end to the beginning of the fillet) is greater than the radius $r_c$ of the hemispherical distal end 220 of the ceramic tip 200. Preferably the length $L_1$ is at least 20% larger than $r_c$. In other words $1.2 r_c < L_1$.

A second preferred embodiment of a ceramic tip in accordance with a preferred embodiment of the present invention is shown in FIGS. 5A-5F. The ceramic tip 500 has a distal portion 510, a proximal portion 520 and a fillet or rounded portion 530 in between the distal and proximal portions. The distal portion preferably is hemispherical in shape. The proximal end of the ceramic tip 500 has a flat circular portion 540 and an opening 550 for receiving a distal end of an electrode. Similar to opening 250 in the first embodiment, the opening 550 may be a cylindrical channel 552 having a rounded end 554. Note that in FIGS. 5A-5F the second embodiment is shown as not having a fillet or rounded edge similar to the fillet 242 in the first embodiment. Such a fillet or rounded edge certainly may be used in the second embodiment or may be excluded in the first embodiment.

Figure 5A:
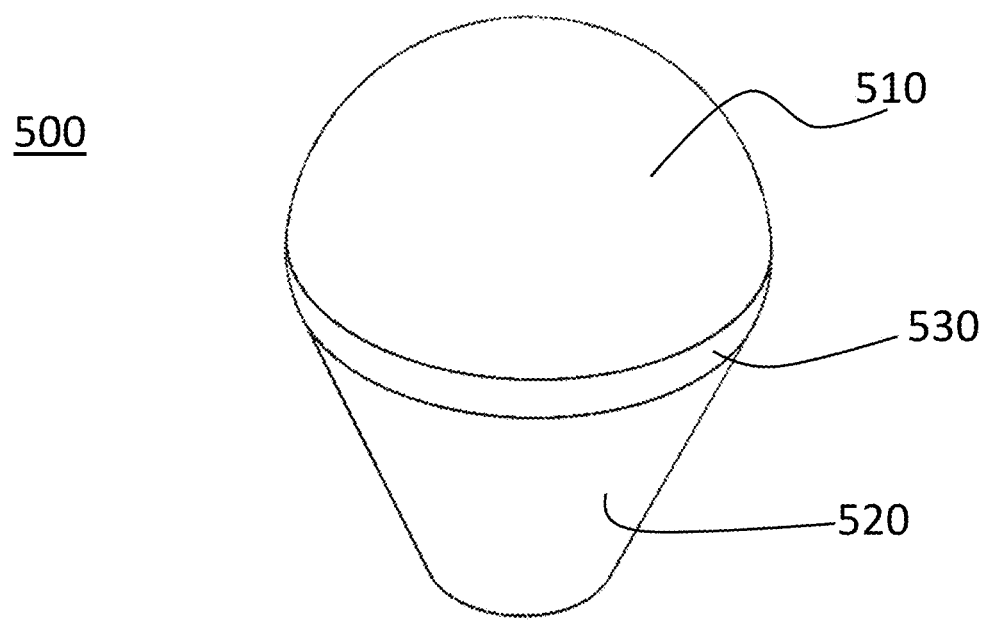
FIG. 5A is a top perspective view of an alternative embodiment of a ceramic tip for a gas-assisted electrosurgical probe in accordance with a preferred embodiment of the present invention.
Figure 5B:
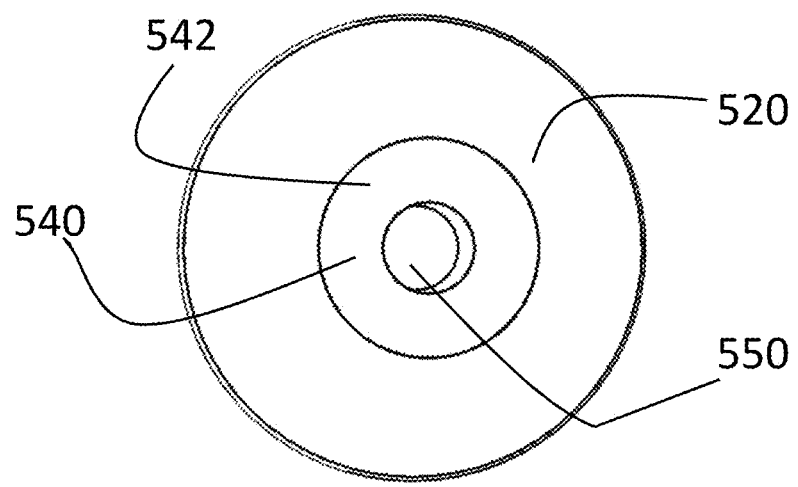
FIG. 5B is a bottom perspective view of an alternative embodiment of a ceramic tip for a gas-assisted electrosurgical probe in accordance with a preferred embodiment of the present invention.
Figure 5C:
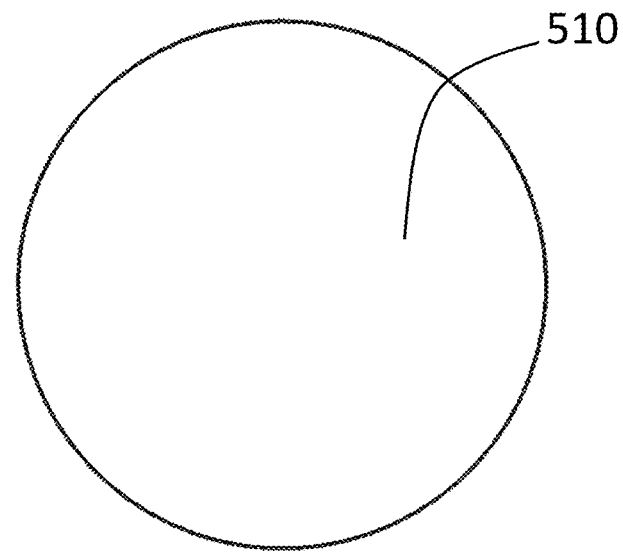
FIG. 5C is a top view of an alternative embodiment of a ceramic tip for a gas-assisted electrosurgical probe in accordance with a preferred embodiment of the present invention.
Figure 5D:
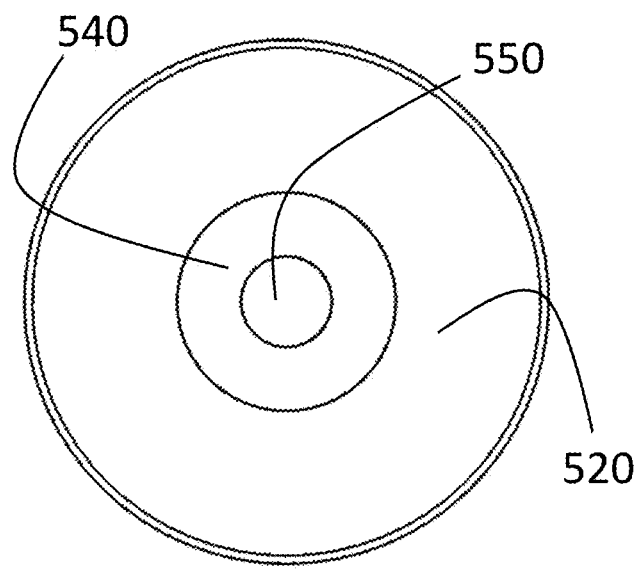
FIG. 5D is a bottom view of an alternative embodiment of a ceramic tip for a gas-assisted electrosurgical probe in accordance with a preferred embodiment of the present invention.
Figure 5E:
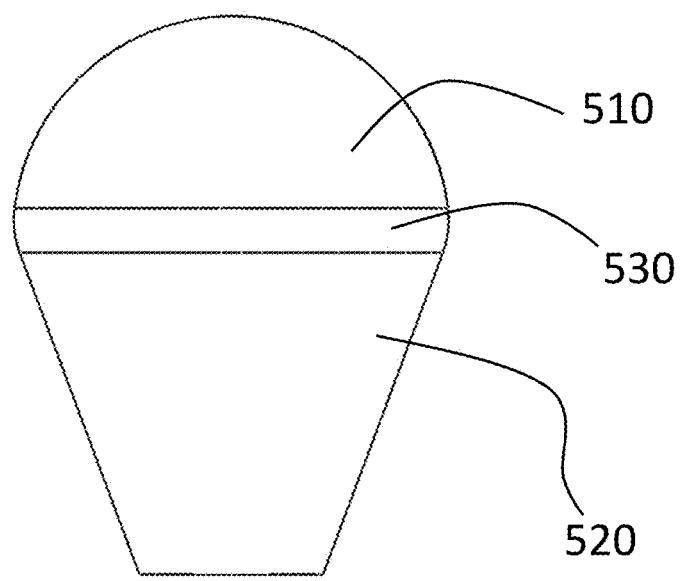
FIG. 5E is a side view of an alternative embodiment of a ceramic tip for a gas-assisted electrosurgical probe in accordance with a preferred embodiment of the present invention.
Figure 5F:
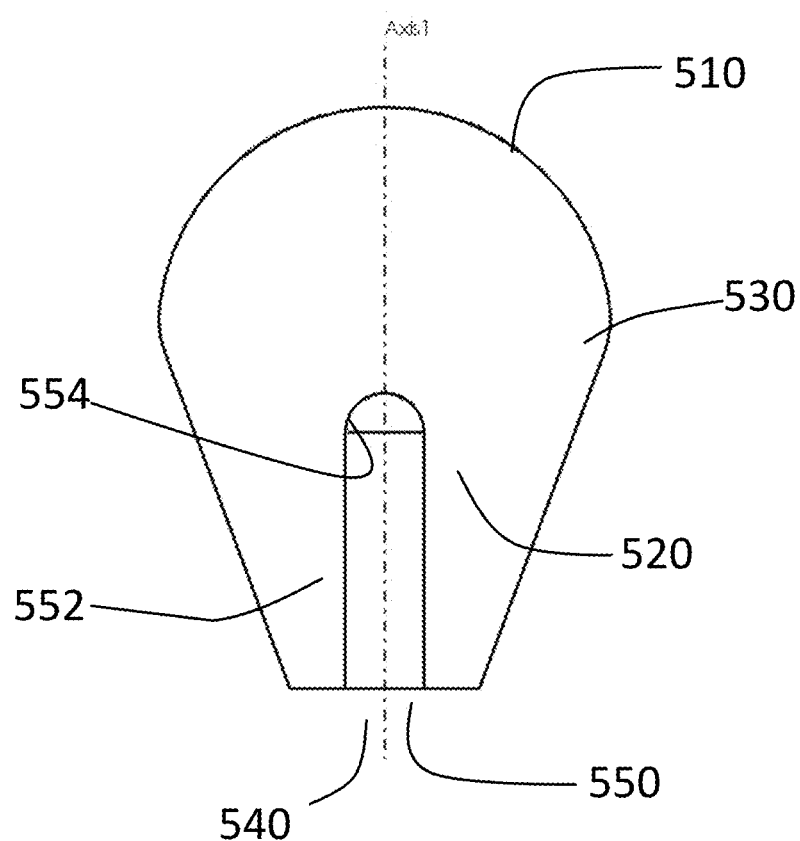
FIG. 5F is a side cross-sectional view of an alternative embodiment of a ceramic tip for a gas-assisted electrosurgical probe in accordance with a preferred embodiment of the present invention.
Figure 6:
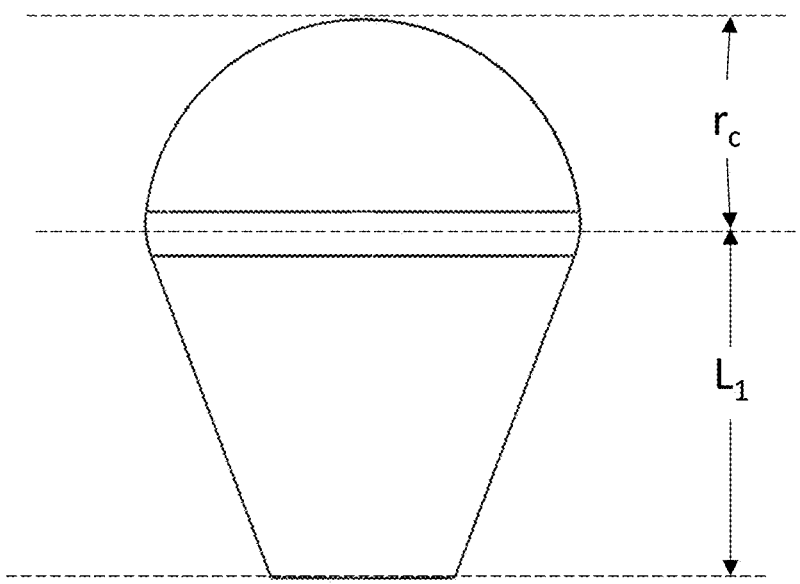
FIG. 6 is a side dimension view of an alternative embodiment of a ceramic tip for a gas-assisted electrosurgical probe with dimensional references in accordance with a preferred embodiment of the present invention.

As shown in FIGS. 5E and 5F, the sides of the proximal portion 520 in the second embodiment are straight rather than curved and thus are not concave or convex. Such straight sides may be said to have an infinite radius of curvature. As shown in FIG. 6, the length $L_1$ of the central axis of the proximal portion 520 of the ceramic tip 500 (from the point at which the hemispherical distal portion 510 would meet the straight proximal portion 520 absent the fillet 530) is greater than the radius $r_c$ of the hemispherical distal end portion 520 of the ceramic tip 500. Preferably the length $L_1$ is at least 20% larger than $r_c$. In other words $1.2r_c<L_1$.

Figure 7:
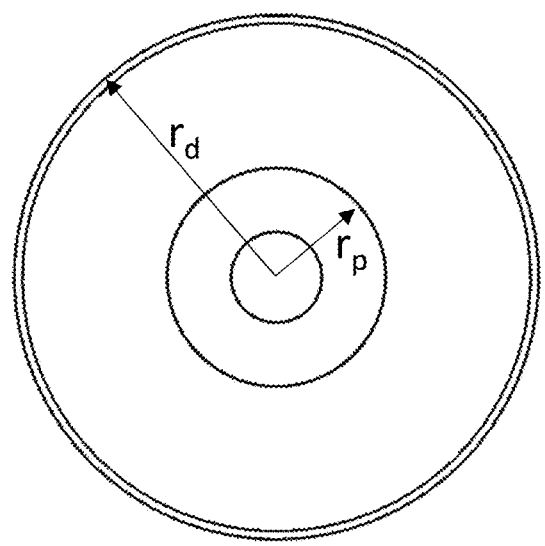
FIG. 7 is a bottom view of a ceramic tip an alternative embodiment of a ceramic tip for a gas-assisted electrosurgical probe with dimensional references in accordance with a preferred embodiment of the present invention.

As shown in FIG. 7, the radius $r_d$ of the distal portion 510 and the radius $r_p$ of the proximal portion along with the length $L_1$ define the slope of the surface of the distal portion 520 as $$\frac{r_d - r_p}{L_1}.$$

Preferably, $r_d>2r_p$ and $$0.9 < \frac{r_d - r_p}{L_1} < 0.5.$$

While the present invention has been described as a ceramic tip, other electrically insulating materials may be used instead of a ceramic material. Thus, the tip of the present invention may be described as an electrically insulating tip for a gas-assisted electrosurgical probe.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A probe for gas-assisted electrosurgery comprising:
    a gas-assisted electrosurgical probe comprising a tube and an electrode within said tube, wherein a distal end portion of said electrode extends from an opening at a distal end of said tube;
    an electrically insulating tip connected to the distal end of said electrode, said electrically insulating tip comprising:
        a substantially hemispherical ceramic distal end portion having a radius $r_c$; and
        a proximal ceramic portion having a circular cross-section, a concave outer surface and a central axis of a length $L_1$;
        wherein $L_1>r_c$.

2. The probe for gas-assisted electrosurgery according to claim 1, further comprising a fillet between said substantially distal end portion and said proximal portion.

3. The probe for gas-assisted electrosurgery according to claim 1, wherein said proximal portion has an outer surface having a plurality of portions with at least two of said plurality of portions having different outer radii of curvature.

4. The probe for gas-assisted electrosurgery according to claim 3, wherein said at least two radii of curvature decrease from a proximal end of said electrically insulating tip to said fillet.

5. The probe for gas-assisted electrosurgery according to claim 1, wherein said proximal portion has an outer surface having a varying radius of curvature.

6. The probe for gas-assisted electrosurgery according to claim 1, wherein said proximal portion has a proximal end having a circular cross-section with a radius $r_p$ and $1.2r_p<L_1$.

7. The probe for gas-assisted electrosurgery according to claim 1, wherein said proximal portion has a proximal end having a circular cross-section with a radius $r_p$ and a distal end with a radius $r_d$, wherein $r_d>2r_p$.

8. The probe for gas-assisted electrosurgery according to claim 1, wherein said proximal portion has a proximal end having a circular cross-section with a radius $r_p$ and a distal end with a radius $r_d$, wherein $$0.9 < \frac{r_d - r_p}{L_1} < 0.5.$$

9. The probe for gas-assisted electrosurgery according to claim 1, wherein said proximal portion has a proximal end having a circular cross-section with a radius $r_p$ and a distal end with a radius $r_d$, wherein $$0.9 < \frac{r_d - r_p}{L_1} < 0.5.$$

* * * * *